(12) United States Patent
Pacetti et al.

(10) Patent No.: US 7,329,413 B1
(45) Date of Patent: Feb. 12, 2008

(54) COATINGS FOR DRUG DELIVERY DEVICES HAVING GRADIENT OF HYDRATION AND METHODS FOR FABRICATING THEREOF

(75) Inventors: Stephen D. Pacetti, San Jose, CA (US); Syed F. A. Hossainy, Fremont, CA (US); Yiwen Tang, San Jose, CA (US); Andrew C. Tung, Castro Valley, CA (US); Thierry Glauser, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 817 days.

(21) Appl. No.: 10/703,334

(22) Filed: Nov. 6, 2003

(51) Int. Cl.
*A61F 2/00* (2006.01)

(52) U.S. Cl. .................................................. 424/423

(58) Field of Classification Search ............... 424/422, 424/423, 469, 470, 489, 698; 428/702, 336; 623/1.44, 1.42, 1.47, 1.46
See application file for complete search history.

(56) References Cited

U.S. PATENT DOCUMENTS

| | | | |
|---|---|---|---|
| 4,329,383 A | 5/1982 | Joh | 428/36 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,941,870 A | 7/1990 | Okada et al. | 600/36 |
| 4,977,901 A | 12/1990 | Ofstead | 128/772 |
| 5,112,457 A | 5/1992 | Marchant | 204/165 |
| 5,165,919 A | 11/1992 | Sasaki et al. | 424/488 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,569,463 A | 10/1996 | Helmus et al. | 424/426 |
| 5,578,073 A | 11/1996 | Haimovich et al. | 623/1 |
| 5,605,696 A | 2/1997 | Eury et al. | 424/423 |
| 5,609,629 A | 3/1997 | Fearnot et al. | 623/1 |
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |

(Continued)

FOREIGN PATENT DOCUMENTS

EP    0 301 856    2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Kevin T. Truong
(74) *Attorney, Agent, or Firm*—Squire, Sanders & Dempsey

(57) ABSTRACT

Coatings for implantable medical devices, and methods for fabricating thereof, are provided. The coatings include a first polymer layer and a second polymer layer, where the second polymer has a higher degree of hydration than the first polymer.

46 Claims, No Drawings

U.S. PATENT DOCUMENTS

| | | | | |
|---|---|---|---|---|
| 6,096,070 | A | 8/2000 | Ragheb et al. | 623/1 |
| 6,099,562 | A | 8/2000 | Ding et al. | 623/1.46 |
| 6,110,188 | A | 8/2000 | Narciso, Jr. | 606/153 |
| 6,110,483 | A | 8/2000 | Whitbourne et al. | 424/423 |
| 6,113,629 | A | 9/2000 | Ken | 623/1.1 |
| 6,120,536 | A | 9/2000 | Ding et al. | 623/1.46 |
| 6,120,904 | A | 9/2000 | Hostettler et al. | 428/423.3 |
| 6,121,027 | A | 9/2000 | Clapper et al. | 435/180 |
| 6,129,761 | A | 10/2000 | Hubbell | 623/11 |
| 6,153,252 | A | 11/2000 | Hossainy et al. | 427/2.3 |
| 6,165,212 | A | 12/2000 | Dereume et al. | 623/1.13 |
| 6,203,551 | B1 | 3/2001 | Wu | 606/108 |
| 6,231,600 | B1 | 5/2001 | Zhong | 623/1.42 |
| 6,240,616 | B1 | 6/2001 | Yan | 29/527.2 |
| 6,245,753 | B1 | 6/2001 | Byun et al. | 514/56 |
| 6,251,136 | B1 | 6/2001 | Guruwaiya et al. | 623/1.46 |
| 6,254,632 | B1 | 7/2001 | Wu et al. | 623/1.15 |
| 6,258,121 | B1 | 7/2001 | Yang et al. | 623/1.46 |
| 6,283,947 | B1 | 9/2001 | Mirzaee | 604/264 |
| 6,283,949 | B1 | 9/2001 | Roorda | 604/288.0 |
| 6,284,305 | B1 | 9/2001 | Ding et al. | 427/2.28 |
| 6,287,628 | B1 | 9/2001 | Hossainy et al. | 427/2.3 |
| 6,299,604 | B1 | 10/2001 | Ragheb et al. | 604/265 |
| 6,306,176 | B1 | 10/2001 | Whitbourne | 623/23.59 |
| 6,331,313 | B1 | 12/2001 | Wong et al. | 424/427 |
| 6,335,029 | B1 | 1/2002 | Kamath et al. | 424/423 |
| 6,346,110 | B2 | 2/2002 | Wu | 606/108 |
| 6,358,556 | B1 | 3/2002 | Ding et al. | 427/2.24 |
| 6,379,381 | B1 | 4/2002 | Hossainy et al. | 623/1.42 |
| 6,395,326 | B1 | 5/2002 | Castro et al. | 427/2.24 |
| 6,419,692 | B1 | 7/2002 | Yang et al. | 623/1.15 |
| 6,451,373 | B1 | 9/2002 | Hossainy et al. | 427/2.25 |
| 6,494,862 | B1 | 12/2002 | Ray et al. | 604/96.01 |
| 6,503,556 | B2 | 1/2003 | Harish et al. | 427/2.24 |
| 6,503,954 | B1 | 1/2003 | Bhat et al. | 514/772.2 |
| 6,506,437 | B1 | 1/2003 | Harish et al. | 427/2.25 |
| 6,527,801 | B1 | 3/2003 | Dutta | 623/1.46 |
| 6,527,863 | B1 | 3/2003 | Pacetti et al. | 118/500 |
| 6,540,776 | B2 | 4/2003 | Sanders Millare et al. | 623/1.15 |
| 6,544,223 | B1 | 4/2003 | Kokish | 604/103.01 |
| 6,544,543 | B1 | 4/2003 | Mandrusov et al. | 424/422 |
| 6,544,582 | B1 | 4/2003 | Yoe | 427/2.24 |
| 6,555,157 | B1 | 4/2003 | Hossainy | 427/2.24 |
| 6,558,733 | B1 | 5/2003 | Hossainy et al. | 427/2.24 |
| 6,565,659 | B1 | 5/2003 | Pacetti et al. | 118/500 |
| 6,572,644 | B1 | 6/2003 | Moein | 623/1.11 |
| 6,585,765 | B1 | 7/2003 | Hossainy et al. | 623/1.45 |
| 6,585,926 | B1 | 7/2003 | Mirzaee | 264/400 |
| 6,605,154 | B1 | 8/2003 | Villareal | 118/500 |
| 6,702,850 | B1 * | 3/2004 | Byun et al. | 623/1.44 |
| 2001/0018469 | A1 | 8/2001 | Chen et al. | 523/121 |
| 2001/0037145 | A1 | 11/2001 | Guruwaiya et al. | 623/1.15 |
| 2002/0077693 | A1 | 6/2002 | Barclay et al. | 623/1.13 |
| 2002/0091433 | A1 | 7/2002 | Ding et al. | 623/1.2 |
| 2002/0155212 | A1 | 10/2002 | Hossainy | 427/2.25 |
| 2003/0065377 | A1 | 4/2003 | Davila et al. | 623/1.13 |
| 2003/0099712 | A1 | 5/2003 | Jayaraman | 424/486 |
| 2003/0118649 | A1 * | 6/2003 | Gao et al. | 424/471 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for* in vivo *delivery to a solid tumor*, Journal of Controlled Release 50:79-92 (1998).

\* cited by examiner

COATINGS FOR DRUG DELIVERY DEVICES HAVING GRADIENT OF HYDRATION AND METHODS FOR FABRICATING THEREOF

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

Local administration of therapeutic agents via stents has shown some favorable results in reducing restenosis. However, these results can be further improved. For example, it is desirable to further improve the overall biocompatibility and non-fouling properties of the stent. It is also desirable to be able to better control the rate of the release of the drug from the coating. The embodiments of the present invention are directed to coatings that satisfy these and other needs.

SUMMARY

According to one embodiment of this invention, a coating for medical devices is provided, the coating includes a first layer comprising a first polymer, and a second layer comprising a second polymer, the second layer being disposed over at least a portion of the first layer, wherein the second polymer has a higher degree of hydration than the first polymer. Optionally, the coating can additionally include a third layer, the third layer comprises a third polymer, the third layer being disposed over at least a portion of the second layer, wherein the third polymer has a higher degree of hydration than the second polymer.

The first polymer can have the degree of hydration between greater than 0% and about 20% by mass. The second polymer can have the degree of hydration between greater than 0% and about 50% by mass. The third polymer can have a degree of hydration between greater than 0% and about 50% by mass. Examples of the first polymer that can be used include polyorthoesters, poly(butyleneterephthalate-co-ethylene glycol), poly(butyl methacrylate), poly(D,L-lactide), poly(caprolactone), poly(4-hydroxybutyrate), poly(3-hydroxybutyrate), poly(hydroxyvalerate), poly(ethylene-co-vinyl alcohol), poly(vinyl alcohol), polybutyral, poly(ethylene-co-vinyl acetate), poly(vinyl acetate), polyurethanes, and blends thereof. Examples of the second and the third polymer that can be used include polyorthoesters, poly(butyleneterephthalate-co-ethylene glycol), and blends thereof. The polyorthoesters that can be used as the first, the second, and the third polymer are products of co-polycondensation of a diketene acetal, a hydroxylated functional compound and a diol. One example of a suitable polyorthoester has the formula

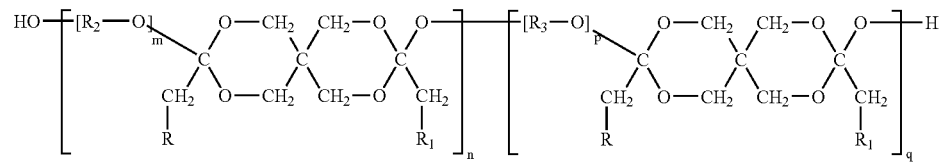

wherein R and $R_1$, is each, independently, an unsusbstituted or substituted straight-chained, branched, or cyclic alkyl radical $C_1$-$C_8$, or unsusbstituted or substituted aryl radical; $R_2$—O is a non-fouling moiety derived from a hydroxylated functional compound; $R_3$ is an aliphatic or cycloaliphatic group; m, n, p, and q are all integers, where the value of m is between 5 and 500, the value of n is between 2 and 350, the value of p is between 1 and 20, and the value of q is between 10 and 550.

A medical article is provided, the medical article comprises an implantable substrate and a coating disposed over at least a portion of the substrate, the coating comprises a first layer and a second layer disposed over at least a portion of the first layer, wherein the second layer has a higher degree of hydration than the first layer.

DETAILED DESCRIPTION

A coating for an implantable medical device, such as a stent, according to embodiments of the present invention, can include any combination of a primer layer, a drug-polymer layer (also referred to as "reservoir" or "reservoir layer"), and a topcoat layer. Possible combination of layers in the stent coating can include:

(a) the primer layer and the reservoir layer without the topcoat layer;

(b) the reservoir layer and the topcoat layer without the primer layer; and (c) all three layers.

The drug-polymer layer serves as a reservoir for the drug. The reservoir layer can be applied directly onto the stent surface. The primer layer can be applied on the stent surface to improve the adhesion of the drug-polymer layer to the stent. The primer layer, if used, is the innermost layer of the coating. The topcoat layer, which can be essentially free from any drugs, can serve as a rate limiting membrane to help control the release of the drug. The topcoat layer can also serve as a non-fouling, or hemocompatible layer, to enhance the biocompatibility of the system. The topcoat layer, if used, can be the outermost layer of the coating.

According to embodiments of the present invention, the layers of the stent are fabricated of polymers which can be hydrated to varying degrees. The terms "hydrated" and "hydration" refer to the ability of a polymer to absorb water at a temperature between the room temperature (e.g., about 20° C.) and the body temperature (about 37° C.) and ambient pressure. To determine the degree of hydration, a polymer can be either immersed in water or exposed to 100% humid atmosphere for a period of time needed to reach the absorption equilibrium (e.g., until the polymer has absorbed maximum possible amount of water).

The degree of hydration for a particular polymer is determined by the polymer's chemical and physical structure. The degree of hydration can be calculated as a ratio between the mass of the water uptake achieved and the total mass of the polymer and water. To illustrate, if 9 grams of a polymer have absorbed 1 gram of water under the above-described conditions, the degree of hydration is 10% by mass. Generally, the polymer included in each layer of the coating can have a degree of hydration between greater than 0 and about 20 mass %, for example, between about 1 mass % and about 6 mass %, such as about 5 mass %. The polymer included in the topcoat layer, if the topcoat layer is used, can have a degree of hydration between greater than 0 and about 50 mass %. Given the polymer and water densities, the degree of hydration by mass can be readily converted to the degree of hydration by volume. The dimensional change in a polymer upon immersion in water can be also used to determine percent hydration by volume.

The coating of the present invention can have a gradient of the concentration of water in the coating. To achieve the gradient, for a stent coating comprising the primer, the drug-polymer and the topcoat layers, a polymer included in the primer can have the lowest degree of hydration of the three layers, the polymer included in the topcoat layer can have the highest degree of hydration, and the polymer included in the drug-polymer layer can have the intermediate degree of hydration. Alternatively, the polymer included in the primer can have the highest degree of hydration of the three layers, the polymer included in the topcoat layer can have the lowest degree of hydration, and the polymer included in the drug-polymer layer can have the intermediate degree of hydration.

As another alternative, the polymers included in the primer and in the drug-polymer layer can have the same degree of hydration, and the polymer included in the topcoat layer can have a degree of hydration that is either higher or lower than that of the polymers included in the primer and the drug-polymer layer. As yet another alternative, the polymers included in the drug-polymer layer and the topcoat layer can have the same degree of hydration, and the polymer included in the primer can have a degree of hydration that is either higher or lower than that of the polymers included in the drug-polymer layer and the topcoat layer.

For a stent coating comprising only the primer and the drug-polymer layer, the polymer included in the primer can have the degree of hydration that is lower than that of the polymer included in the drug-polymer layer. In another embodiment, for a stent coating comprising only the primer and the drug-polymer layers, the polymer included in the primer can have the degree of hydration that is higher than that of the polymer included in the drug-polymer layer.

For a stent coating comprising only the drug-polymer and the topcoat layer, the polymer included in the drug-polymer layer can have the degree of hydration that is lower than that of the polymer included in the topcoat layer. In another embodiment, for a stent coating comprising only the drug-polymer and the topcoat layers, the polymer included in the drug-polymer layer can have the degree of hydration that is higher than that of the polymer included in the topcoat layer.

Examples of polymers that can be used to fabricate the primer layer include polyorthoesters, poly(butyleneterephthalate-co-ethylene glycol) (PBT-PEG), poly(ethylene glycol)-block-poly(butyleneterephthalate)-block poly(ethylene glycol) (PEG-PBT-PEG or POLYACTIVE), poly(n-butyl methacrylate)(PBMA), poly(D,L-lactide), poly(caprolactone), poly(4-hydroxybutyrate), poly(3-hydroxybutyrate), poly(hydroxyvalerate), poly(ethylene-co-vinyl alcohol), poly(vinyl alcohol), polybutyral, poly(ethylene-co-vinyl acetate), poly(vinyl acetate), polyurethanes, and blends thereof.

POLYACTIVE is a trade name of a family of PEG-PBT-PEG polymers and is available from IsoTis Corp. of Holland. In various grades of POLYACTIVE, the ratio between the units derived from ethylene glycol and the units derived from butyleneterephthalate can be between about 0.67:1 and about 9:1. The molecular weight of the units derived from ethylene glycol can be between about 300 Daltons and about 4,000 Daltons. The overall weight-averaged molecular weight ($M_w$) of the POLYACTIVE polymers can be between about 75,000 Daltons and about 125,000 Daltons. To make the primer, a grade of POLYACTIVE can be used having a molecular weight of the ethylene glycol-derived units of about 300 and having a ratio between the ethylene glycol-derived units and the butylene terephthalate-derived units of about 1.22:1 (about 55:45).

Examples of polymers that can be used for fabricating the drug-polymer layer include polyorthoesters, PBT-PEG, POLYACTIVE, poly(n-butyl methacrylate), poly(ethyl methacrylate), poly(methyl methacrylate), poly(n-propyl methacrylate), other polymethacrylates, poly(D,L-lactide), poly(caprolactone), poly(4-hydroxybutyrate), poly(3-hydroxybutyrate), poly(hydroxyvalerate), poly(ethylene-co-vinyl alcohol), poly(vinyl alcohol), poly(ethylene-co-vinyl acetate), poly(vinyl acetate), poly(vinylidene fluoride), poly (vinylidene fluoride-co-hexafluoropropene), poly(vinylidene fluoride-co-chlorotrifluoroethylene), polyurethanes, and blends thereof. The same or a different grade of POLYACTIVE can be used as the one used for making the primer.

Examples of polymers that can be used for fabricating the topcoat layer include polyorthoesters, PBT-PEG, POLYAC- TIVE, polyorthoesters with poly(ethylene glycol)(PEG) incorporated into the polymer backbone, copolymers of alkyl methacrylates and 2-hydroxyethyl methacrylate, copolymers of PEG-acrylates and alkyl methacrylates, copolymers of PEG-methacrylates and alkyl methacrylates, poly(ester-amides) with PEG functionality, derivatives of hyaluronic acid, heparin conjugates, sulfonated polystyrenes, and poly(ethylene-co-vinyl alcohol) with pendant PEG functionality. To make the topcoat layer, a grade of POLYACTIVE can be used having the molecular weight of the ethylene glycol-derived units of about 4,000 and having the ratio between the ethylene glycol-derived units and the butylene terephthalate-derived units of about 4:1 (about 80:20).

[5,5]-undecane (DETOSU), 3,9-dipentylidene-2,4,8,10-tetraoxaspiro-[5,5]-heptadecane (DPTOSH), 3,9-dibutylidene-2,4,8,10-tetraoxaspiro-[5,5]-pentadecane, 3,9-dipropylidene-2,4,8,10-tetraoxaspiro-[5,5]-tridecane and mixtures thereof. Those having ordinary skill in the art can synthesize diketene acetals, as described in the literature, for example, in Heller *J, Adv. Polymer Sci., vol.* 107, pp. 41-92 (1993).

If both R and $R_1$ in formula (I) are methyl groups, formula (I) describes the molecule of DETOSU. For DPTOSH, both R and $R_1$ in formula (I) are n-butyl groups.

Consequently, DETOSU has the formula (IIA) and DPTOSH has the formula (IIB):

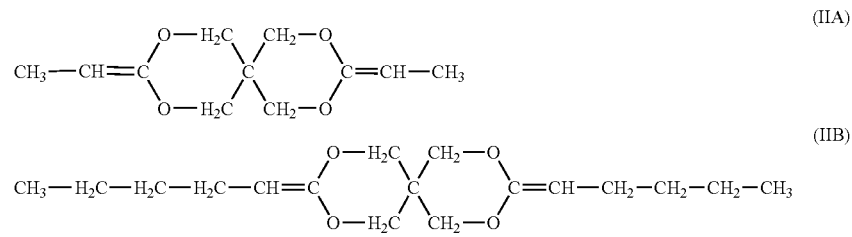

As indicated above, polyorthoesters are one class of polymers that can be used to make any or all of the layers. The polyorthoesters that are suitable for making stent coatings are products of co-polycondensation of at least one compound of Group I (a diketene acetal) with at least one compound of Group II (a hydroxy functional compound) and with at least one compound of Group III (a diol). Groups I, II, and III, and particular compounds that are included in these Groups are described below.

By selecting particular compounds of each of the Groups I, II and III, polyorthoesters having any desired degree of hydration can be synthesized. Following the synthesis, the polyorthoester can be used to make a particular coating layer in accordance with the degree of hydration of the polyorthoester. Thus, polyorthoesters having the degree of hydration less than 10 vol. % can be used to make the primer, the polyorthoesters having the degree of hydration between 0.5 and 10 vol. % can be used to make the drug-polymer layer, and the polyorthoesters having the degree of hydration more than 10 vol. % can be used to make the topcoat.

Group I. Diketene Acetals

Diketene Acetals have a general formula (I)

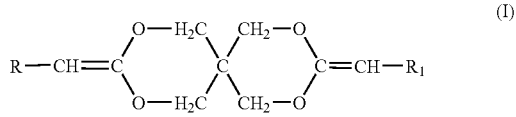

where R and $R_1$ can be, independently, unsusbstituted or substituted straight-chained, branched, or cyclic alkyl radicals $C_1$-$C_8$, or unsusbstituted or substituted aryl radicals. Any suitable substitutent to be selected by those having ordinary skill in the art can be present in the substituted radicals.

Examples of diketene acetals described by formula (I) that can be used include 3,9-diethylidene-2,4,8,10-tetraoxaspiro- Group II. Hydroxy Functional Compounds Group II comprises hydroxylated compounds having at least one hydroxyl group. The hydroxyl group can be located in a terminal or non-terminal position of the molecule. Examples of hydroxy functional compounds that can be used include poly(alkylene glycols), for example, poly(ethylene glycol) (PEG), poly(propylene glycol) (PPG) or poly (tetramethylene glycol), PLURONIC surfactants, hydroxylated poly(vinyl pyrrolidone), dextran, dextrin, hyaluronic acid and derivatives thereof, such as sodium hyaluronate, and poly(2-hydroxyethyl methacrylate), or mixtures thereof. PLURONIC is a trade name of poly(ethylene oxide-co-propylene oxide) and is available from BASF Corp. of Parsippany, N.J.

A molecular weight of a suitable compound of Group II can be such so as to allow passage of the released molecule through the kidneys, for example, below 40,000 Daltons, such as between about 300 and 20,000 Daltons.

Compounds of Group II can be described by a general formula (III):

where "m" is an integer, and —$R_2$—O— represents the moiety of compound (III) providing non-fouling characteristics. For example, when compound (III) is a poly(alkylene glycol), $R_2$ is the polymethylene structure $(CH_2)_x$, where "x" is an integer. To illustrate, in case of compound (III) being PEG, x=2.

Group III. Diols

Group III comprises short-to-moderate-length (e.g., $C_1$ through $C_{16}$) aliphatic or cycloaliphatic diols or blends or combinations thereof. Examples of diols that can be used include alkylene glycols, for example, $C_2$ through $C_{16}$ α,ω-glycols such as ethylene glycol ($C_2$), propane-1,2-diol ($C_3$), propane-1,3-diol ($C_3$), butane-1,4-diol ($C_4$), pentane-1,5-diol ($C_5$), hexane-1,6-diol ($C_6$), heptane-1,7-diol (C7), octane-1,8-diol (C8), nonane-1,9-diol ($C_9$), decane-1,10-diol ($C_{10}$), undecane-1,11-diol ($C_{11}$), dodecane-1,12-diol ($C_{12}$), tridecane-1,13-diol ($C_{13}$), tetradecane-1,14-diol ($C_{14}$), pentadecane-1,15-diol ($C_{15}$), hexadecane-1,16-diol ($C_{16}$), or mixtures thereof, or other alkylene glycols, for example, butane-1,3-diol, pentane-2,4-diol, hexane-2,5-diol, or mixtures thereof. Other aliphatic diols that can be used include oligoalkylene glycols such as diethylene glycol, trimethylene glycol, tetramethylene glycol, tetraethylene glycol, poly(tetraethylene glycol), poly(propylene glycol), and mixtures thereof. Examples of cycloaliphatic diols that can be used include trans-cyclohexanedimethanol, 1,4-cyclohexanediol, and mixtures thereof.

Compounds of Group III can be described by a general formula (IV):

where $R_3$ represents an aliphatic or cycloaliphatic group. For example, when compound (IV) is an alkylene glycol, $R_3$ is the poly- or oligomethylene structure $(CH_2)_y$, where "y" is an integer between 2 and 16. To illustrate, when compound (IV) is ethylene glycol, y=2. In case of propane-1,3-diol ($C_3$), y=3.

One way of preparing polyorthoesters is a to use a two-step synthetic process. The first step includes reacting the whole amount of diketene acetal of Group I with a hydroxy functional compound of Group II. The reaction ("reaction 1") can be conducted in anhydrous environment at an elevated temperature, for example, about 80° C., and can be catalyzed by a strong acid or base, e.g., p-toluenesulfonic acid. The second step includes adding a diol of Group III to the product of reaction 1, which can be conducted at an elevated temperature, for example, about 80° C. As a result of the two-step process described above, a polyorthoester can be obtained, the polyorthoester having a general formula (V):

molecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides, such as polyvinylidene fluoride, poly(vinylidene fluoride-co-hexafluoropropene), poly(vinylidene fluoride-co-chlorotrifluoroethylene) and polyvinylidene chloride; polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich, or COSMEGEN available from Merck). Synonyms of actinomycin D include dactino-

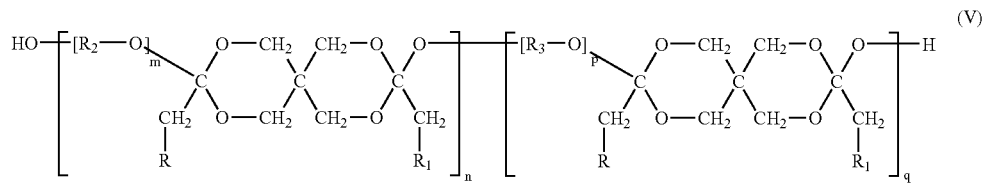

where R, $R_1$, $R_2$, and $R_3$ are as described above; m, n, p, and q are all integers, where the value of m is between about 5 and about 500, the value of n is between about 2 and about 350, the value of p is between about 1 and about 20, and the value of q is between about 10 and about 550. The polyorthoester described by formula (V) can have molecular weight within a range of between about 20,000 and about 200,000 Daltons.

In addition, other (alternative) polymers can be used to make the stent coatings. The alternative polymers can be used instead of, or in a combination with, the above-described polymers. A variety of the alternative polymers can be used so long as the degree of hydration of the alternative polymer is within the limits specified above for the primer, drug-polymer and/or the topcoat layer.

Representative examples of other polymers that can be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomycin, actinomycin IV, actinomycin II, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O—[2-(2-hydroxy)ethoxy]ethyl-rapamycin, and 40-O-tetrazole-rapamycin.

The stent, or other implantable medical device can be used in any part of the vascular system, including neurological, carotid, coronary, renal, aortic, iliac, femoral or any other part of the peripheral vasculature. The are no limitations on the size of the stent, its length, diameter, strut thickness or pattern. Examples of such implantable devices include self-expandable stents, balloon-expandable stents, stent-grafts, grafts (e.g., aortic grafts). The coating can also be used with artificial heart valves, cerebrospinal fluid shunts, coronary shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), cobalt chromium alloy L-605, stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The following examples demonstrate some embodiments of the present invention.

EXAMPLE 1

Synthesis of poly(ethylene glycol-co-3,9-diethylidene-2,4,8,10-tetraoxaspiro-[5,5]-undecane-co-1,4-butanediol) (PEG-DETOSU-BD)

About 25 g (12.5 mmol) of PEG having molecular weight ($M_w$) of about 2,000 can be placed into a 1-liter round bottom flask equipped with a mechanical stirrer. PEG can be treated to remove water by being heated to about 80° C. using an oil bath, while being stirred under vacuum of about 25 mm Hg. About 400 g of tetrahydrofuran (THF) and about 5.74 g (27.08 mmol) of DETOSU can be added to the flask and dissolved with continued stirring. A solution of p-toluenesulfonic acid in THF having concentration of about 25 g/l can be prepared and about 10 drops of this solution can be added to the contents of the flask. The stirring can continue for about 1 hour while the contents of the flask are maintained at about 80° C. About 8.53 g (16.67 mmol) of 1,4-butanediol can then be added to the flask, and the stirring can continue for about 1 more hour while the contents of the flask are continued to be kept at about 80° C. The reaction mixture then can be cooled and about 1 liter of hexane can be added. As a result, the polyorthoester PEG-DETOSU-BD, can be collected by filtration. The polymer can then be purified by dissolution in dry methanol or chloroform and precipitated with hexane.

The structure of PEG-DETOSU-BD can be described by formula (VI)

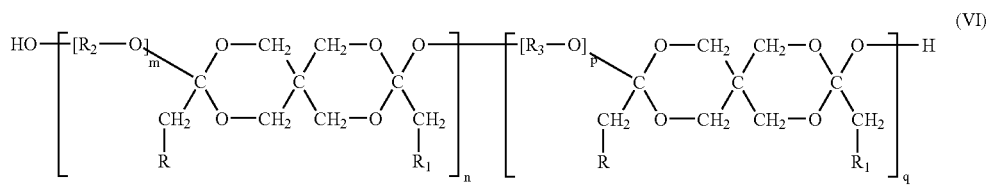

where R and $R_1$ is each $CH_3$, $R_2$ is $(CH_2)_2$, $R_3$ is $(CH_2)_4$, m=45, n=13, p=1, and q=17 (the values of m, n, p, and q are rounded to the nearest integer). PEG-DETOSU-BD is quite hydrophilic and is expected to have the degree of hydration of between about 25 vol. % and about 50 vol. %, for example, about 40 vol. %.

EXAMPLE 2

Synthesis of poly(trans-cyclohexanedimethanol)-co-3,9-diethylidene-2,4,8,10-tetraoxaspiro-[5,5]-undecane-co-1,6-hexanediol) (CHDM-DETOSU-HD)

A poly(ortho ester) can be synthesized of DETOSU and a diol component. The diol component can comprise a mixture of trans-cyclohexanedimethanol (CHDM) and 1,6-hexanediol (HD), the mixture having the molar ratio between CHDM and HD of about 7:3. A synthesis method described in Example 1 can be used. CHDM-DETOSU-HD is quite hydrophobic and is expected to have the degree of hydration of less than about 1 vol. %.

EXAMPLE 3

Synthesis of poly(3,9-diethylidene-2,4,8,10-tetraoxasipiro-[5,5]-undecane-co-1,10-decanediol (DETOSU-DD)

About 13.94 g (80 mmol) of 1,10-decanediol can be placed into a 500 ml round bottom flask equipped with a mechanical stirrer. Water can be removed form the diol by heating it above melting to about 80° C. using an oil bath, while being stirred under a vacuum of about 25 mm Hg. About 100 ml of THF and about 16.98 g (80 mmol) of DETOSU can be added to the flask and dissolved with stirring. A solution of p-toluenesulphonic acid in THF having a concentration of about 1 mass % can be prepared and about 12 drops of this solution can be added to the contents of the flask. The stirring can continue for about 1 hour while the contents of the flask are maintained at about 80° C. The reaction mixture can be cooled and the polymer isolated on a rotoevaporator. The polymer can then be purified by dissolution in dry methanol or chloroform, followed by precipitation with hexane. DETOSU-DD is quite hydrophobic and is expected to have a degree of hydration of less than about 1 vol. %.

EXAMPLE 4

A first composition can be prepared by mixing the following components:

(a) about 2.0 mass % CHDM-DETOSU-HD synthesized as described in Example 2; and (b) the balance, a solvent blend of trichloroethane and tetrahydrofuran at a mass ratio of about 1:1.

The first composition can be applied onto the surface of a bare 18 mm VISION stent (available from Guidant Corp.) by spraying and dried to form a primer layer. An EFD spray head can be used, having a 0.014 inch round nozzle tip and a 0.028 inch round air cap with a feed pressure of about 0.2 atm (3 psi) and an atomization pressure of between about 1 atm and 1.3 atm (15 to 20 psi). The total amount of solids of the primer layer can be about 120 micrograms (µg). After spraying, the stents can be baked at about 55° C. for about one hour.

"Solids" means the amount of dry residue deposited on the stent after all volatile organic compounds (e.g. the solvent) have been removed.

A second composition can be prepared by mixing the following components:

(a) about 4 mass % DETOSU-DD synthesized as described in Example 3;

(b) about 1 mass % EVEROLIMUS; and (c) the balance, a solvent blend of trichloroethane and tetrahydrofuran at a mass ratio of about 1:1.

The second composition can be applied onto the dried primer to form a drug-polymer layer, using the same spraying technique and equipment used for applying the primer layer. Solvent can be removed by baking at about 50° C. for about one hour. The total amount of solids of the drug-polymer layer can be about 832 µg.

A third composition can be prepared by mixing the following components:

(a) about 2 mass % PEG-DETOSU-BD obtained as described in Example 1;

(b) the balance, a solvent blend of acetone and cyclohexanone at a mass ratio of about 1:1.

The third composition can be applied onto the dried reservoir layer, using the same spraying technique and equipment used for applying the primer and drug-polymer layers to form a topcoat layer. Solvent can be removed by baking at 50° C. for one hour. The total amount of solids of the topcoat layer can be about 100 µg.

EXAMPLE 5

A first composition can be prepared by mixing the following components:

(a) about 2.0 mass % PEG-PBT-PEG (POLYACTIVE); and (b) the balance, a solvent blend, the blend comprising 1,1,2-tricloroethane and chloroform in a mass ratio between 1,1,2-tricloroethane and chloroform of about 4:1.

The grade of POLYACTIVE that can be used can have about 45 molar % units derived from PBT and about 55 molar % units derived from PEG. The molecular weight of the PEG units can be about 300 Daltons. The overall weight-averaged molecular weight ($M_w$) of POLYACTIVE can be between about 75,000 Daltons and about 125,000 Daltons. The first composition can be applied onto the surface of a bare 12 mm VISION stent (available from Guidant Corporation) by spraying, using the spraying technique and equipment described in Example 4 and dried to form a primer layer. The primer can be baked at about 140° C. for about 1 hour to yield a dry primer layer having solids content of about 100 µg.

A second composition can be prepared by mixing the following components:

(a) about 2 mass % POLYACTIVE;

(b) about 1 mass % paclitaxel; and (c) the balance, the blend of 1,1,2-tricloroethane and chloroform described above.

The same grade of POLYACTIVE as that utilized for making the primer layer can be used. The second composition can be applied onto the dried primer layer, using the same spraying technique and equipment used for applying the primer layer, to form the drug-polymer layer. The second composition can be baked at about 50° C. for about 1 hour, yielding a dry drug-polymer layer having solids content of about 400 µg.

A third composition can be prepared by mixing the following components:

(a) about 2.0 mass % POLYACTIVE having about 45 molar % units derived from PBT and about 55 molar % units derived from PEG, as described above;

(b) about 2.0 mass % POLYACTIVE having about 20 molar % units derived from PBT and about 80 molar % units derived from PEG, where the molecular weight of the PEG units can be about 4,000 Daltons and the overall $M_w$ of this grade of POLYACTIVE can be between about 75,000 Daltons and about 125,000 Daltons; and (c) the balance, the blend of 1,1,2-tricloroethane and chloroform described above.

The third composition can be applied onto the dried drug-polymer layers, using the same spraying technique and equipment used for applying the primer land drug-polymer layers, to form a topcoat layer. The third composition can be baked at about 50° C. for about 2 hours, yielding a dry topcoat layer having solids content of about 100 µg.

EXAMPLE 6

A first composition can be prepared by mixing the following components:

(a) about 2.0 mass % poly(n-butyl methacrylate) (PBMA); and (b) the balance, a solvent bland comprising acetone and cyclohexanone in a mass ratio of about 1:1.

The PBMA solution can be applied onto the surface of a bare 18 mm VISION stent by spraying, using the spraying technique and equipment described in Example 4, and dried to form a primer layer. The primer layer can be baked at about 80° C. for about 30 minutes to yield a dry primer layer having solids content of about 120 µg.

A second composition can be prepared by mixing the following components:

(a) about 3 mass % poly(n-butyl methacrylate-co-(2-hydroxyethyl)methacrylate) having about 80 mass % of the units derived from n-butyl methacrylate, and the balance, the units derived from (2-hydroxyethyl)methacrylate;

(b) about 1 mass % EVEROLIMUS; and (c) the balance, a solvent blend comprising dimethylacetamide and acetone in a mass ratio of about 7:3.

The second composition can be applied onto the dried primer layer, using the same spraying technique and equipment used for applying the primer layer, to form the drug-polymer layer. The second composition can be baked at about 50° C. for about 1 hour, yielding a dry drug-polymer layer having solids content of about 640 μg.

Next, a methoxy terminated poly(ethylene glycol)-block-co-poly(n-butyl methacrylate) (mPEG-PBMA) can be synthesized. mPEG-PBMA is an AB block copolymer. The term "AB block copolymer" is defined as a block-copolymer contain polymeric moieties A and B. The AB block-copolymers can be described by the formula $[-A-A-A]_m-[B-B-B-]_n$, where each of "m" and "n," is an integer greater than 0. The blocks of the AB block copolymers need not be linked on the ends, since the values of "m" and "n" are such as to ensure that the individual blocks are usually long enough to be considered polymers in their own right. In mPEG-PBMA, A is a poly(ethylene glycol) moiety, and B is a PBMA moiety. mPEG is available from Nektar Corp. (formerly, Shearwater Corp.) of Huntsville, Ala.

Those having ordinary skill in the art, can use a variety of synthetic techniques to prepare mPEG-PBMA. One synthetic method that can be used includes a two-step process. First, mPEG having molecular weight of about 5,000 can be functionalized with 2-bromoisobutyryl bromide. The path of functionalization is expected to include a reaction of terminal hydroxyl of mPEG with bromoisobutyryl bromide, yielding a brominated derivative of mPEG, as shown by the reaction scheme (VII):

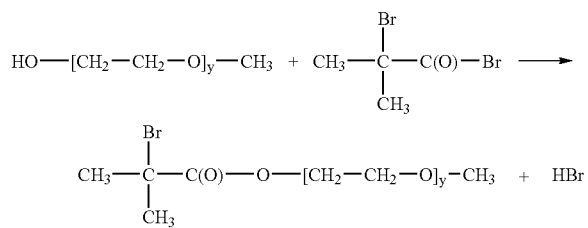

(VII)

The process of functionalization is followed by copolymerization of n-butyl with methacrylate the ester that is a product of the reaction (VII). The step of copolymerization can be carried as living copolymerization catalyzed by copper bromide-amine ligand complex, as known to those having ordinary skill in the art. The synthesis yields mPEG-PBMA AB block copolymer, the structure of which can be illustrated by the formula (VIII):

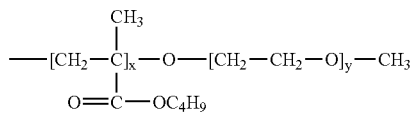

(VIII)

A third composition can be prepared by mixing the following components:

(a) about 2.0 mass % mPEG-PBMA of formula (VII) synthesized, as described above, having the $M_w$ between about 100,000 Daltons and about 250,000 Daltons; and (c) the balance, a solvent blend comprising 1,1,2, trichloroethane and chloroform in a mass ratio of about 1:1.

The third composition can be applied onto the dried drug-polymer layers, using the same spraying technique and equipment used for applying the primer and drug-polymer layers, to form a topcoat layer. The third composition can be baked at about 80° C. for about 30 minutes, yielding a dry topcoat layer having solids content of about 120 μg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, including a first layer comprising a first polymer, and a second layer comprising a second polymer, the second layer being disposed over at least a portion of the first layer, wherein the second polymer has a higher degree of hydration than the first polymer, and wherein the first polymer or the second polymer comprises a polyorthoester.

2. The coating of claim 1, wherein the implantable medical device is a stent.

3. The coating of claim 1, wherein the degree of hydration of the first polymer is between greater than 0% and about 20% by mass.

4. The coating of claim 1, wherein the degree of hydration of the second polymer is between greater than about 0% and about 50% by mass.

5. The coating of claim 1, wherein the first polymer is selected from a group consisting of polyorthoesters, poly(butyleneterephthalate-co-ethylene glycol), poly(ethylene glycol)-block-poly(butyleneterephthalate)-block poly(ethylene glycol), poly(n-butyl methacrylate), poly(D,L-lactide), poly(caprolactone), poly(4-hydroxybutyrate), poly(3-hydroxybutyrate), poly(hydroxyvalerate), poly(ethylene-co-vinyl alcohol), poly(vinyl alcohol), polybutyral, poly(ethylene-co-vinyl acetate), poly(vinyl acetate), polyurethanes, and blends thereof.

6. The coating of claim 5, wherein the polyorthoesters are products of co-polycondensation of a diketene acetal, a hydroxylated functional compound and a diol.

7. The coating of claim 6, wherein the diketene acetal has a formula

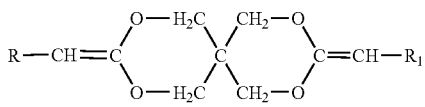

wherein R and $R_1$ are, independently, unsusbstituted or substituted straight-chained, branched, or cyclic alkyl radicals $C_1$-$C_8$, unsusbstituted aryl radicals, or substituted aryl radicals.

8. The coating of claim 6, wherein the diketene acetal is selected from a group consisting of 3,9-diethylidene-2,4,8,10-tetraoxaspiro-[5,5]-undecane, 3,9-dipentylidene-2,4,8,10-tetraoxaspiro-[5,5]-heptadecane, 3,9-dibutylidene-2,4,8,10-tetraoxaspiro-[5,5]-pentadecane, 3,9-dipropylidene-2,4,8,10-tetraoxaspiro-[5,5]-tridecane, and mixtures thereof.

9. The coating of claim 6, wherein the hydroxylated functional compound comprises poly(alkylene glycols), hydroxylated poly(vinyl pyrrolidone), dextran, dextrin, hyaluronic acid, derivatives of hyaluronic acid, poly(2-hydroxyethyl methacrylate), or mixtures thereof.

10. The coating of claim 9, wherein poly(alkylene glycols) are selected from a group consisting of poly(ethylene glycol), poly(propane-1,2-diol), poly(propane-1,3-diol), poly(tetramethylene glycol), and poly(ethylene oxide-co-propylene oxide).

11. The coating of claim 6, wherein the diol comprises alkylene glycols, oligoalkylene glycols, or cycloaliphatic diols.

12. The coating of claim 11, wherein alkylene glycols are selected from a group consisting of ethylene glycol, propane-1,2-diol, propane-1,3-diol, butane-1,4-diol, pentane-1,5-diol, hexane-1,6-diol, heptane-1,7-diol, octane-1,8-diol, nonane-1,9-diol, decane-11,10-diol, undecane-1,11-diol, dodecane-1,12-diol, tridecane-1,13-diol, tetradecane-11,14-diol, pentadecane-1,15-diol, hexadecane-1,16-diol, butane-1,3-diol, pentane-2,4-diol, hexane-2,5-diol, or mixtures thereof.

13. The coating of claim 11, wherein oligoalkylene glycols are selected from a group consisting of diethylene glycol, trimethylene glycol, tetramethylene glycol, tetraethylene glycol, poly(tetraethylene glycol), poly(propylene glycol), and mixtures thereof.

14. The coating of claim 11, wherein cycloaliphatic diols are selected from a group consisting of trans-cyclohexanedimethanol, 1,4-cyclohexanediol, and mixtures thereof.

15. The coating of claim 1, wherein the second polymer is selected from a group consisting of polyorthoesters, poly(butyleneterephthalate-co-ethylene glycol), poly(ethylene glycol)-block-poly(butyleneterephthalate)-block poly(ethylene glycol), poly(n-butyl methacrylate), poly(ethyl methacrylate), poly(methyl methacrylate), poly(n-propyl methacrylate), other polymethacrylates, poly(D,L-lactide), poly(caprolactone), poly(4-hydroxybutyrate), poly(3-hydroxybutyrate), poly(hydroxyvalerate), poly(ethylene-co-vinyl alcohol), poly(vinyl alcohol), poly(ethylene-co-vinyl acetate), poly(vinyl acetate), poly(vinylidene fluoride), poly(vinylidene fluoride-co-hexafluoropropene), poly(vinylidene fluoride-co-chlorotrifluoroethylene), polyurethanes, and blends thereof.

16. The coating of claim 15, wherein the polyorthoesters are products of co-polycondensation of a diketene acetal, a hydroxylated functional compound and a diol.

17. The coating of claim 16, wherein the diketene acetal has a formula

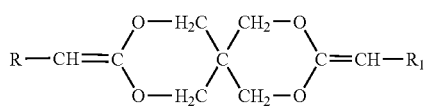

wherein R and $R_1$ are, independently, unsusbstituted or substituted straight-chained, branched, or cyclic alkyl radicals $C_1$-$C_8$, unsusbstituted aryl radicals, or substituted aryl radicals.

18. The coating of claim 16, wherein the diketene acetal is selected from a group consisting of 3,9-diethylidene-2,4,8,10-tetraoxaspiro-[5,5]-undecane, 3,9-dipentylidene-2,4,8,10-tetraoxaspiro-[5,5]-heptadecane, 3,9-dibutylidene-2,4,8,10-tetraoxaspiro-[5,5]-pentadecane, 3,9-dipropylidene-2,4,8,10-tetraoxaspiro-[5,5]-tridecane, and mixtures thereof.

19. The coating of claim 16, wherein the hydroxylated functional compound comprises poly(alkylene glycols), hydroxylated poly(vinyl pyrrolidone), dextran, dextrin, hyaluronic acid, derivatives of hyaluronic acid, poly(2-hydroxyethyl methacrylate), or mixtures thereof.

20. The coating of claim 19, wherein poly(alkylene glycols) are selected from a group consisting of poly(ethylene glycol), poly(propylene glycol), poly(tetramethylene glycol), and poly(ethylene oxide-co-propylene oxide).

21. The coating of claim 16, wherein the diol comprises alkylene glycols, oligoalkylene glycols, or cycloaliphatic diols.

22. The coating of claim 21, wherein alkylene glycols are selected from a group consisting of ethylene glycol, propane-1,2-diol, propane-1,3-diol, butane-1,4-diol, pentane-1,5-diol, hexane-1,6-diol, heptane-1,7-diol, octane-1,8-diol, nonane-1,9-diol, decane-1,10-diol, undecane-1,11-diol, dodecane-1,12-diol, tridecane-1,13-diol, tetradecane-1,14-diol, pentadecane-1,15-diol, hexadecane-1,16-diol, butane-1,3-diol, pentane-2,4-diol, hexane-2,5-diol, or mixtures thereof.

23. The coating of claim 21, wherein oligoalkylene glycols are selected from a group consisting of diethylene glycol, trimethylene glycol, tetramethylene glycol, tetraethylene glycol, poly(tetraethylene glycol), poly(propylene glycol), and mixtures thereof.

24. The coating of claim 21, wherein cycloaliphatic diols are selected from a group consisting of trans-cyclohexanedimethanol, 1,4-cyclohexanediol, and mixtures thereof.

25. The coating of claim 1, wherein the first polymer is a polymer having a formula

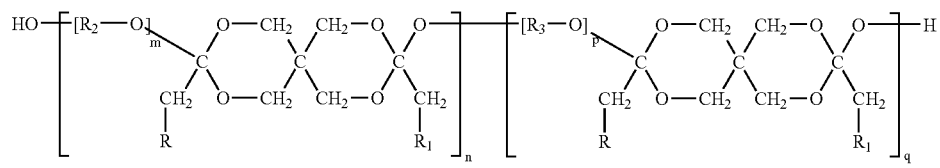

wherein R and $R_1$, is each, independently, an unsusbstituted or substituted straight-chained, branched, or cyclic alkyl radical $C_1$-$C_8$, unsusbstituted aryl radical or substituted aryl radical;

$R_2$—O is a non-fouling moiety derived from a hydroxylated functional compound;

$R_3$ is an aliphatic or cycloaliphatic group; and m, n, p, and q are all integers, wherein the value of m is between 5 and 500, the value of n is between 2 and 350, the value of p is between 1 and 20, and the value of q is between 10 and 550.

26. The coating of claim 25, wherein $R_2$ is a poly(methylene oxide structure).

27. The coating of claim 25, wherein the hydroxylated functional compound comprises poly(alkylene glycols), hydroxylated poly(vinyl pyrrolidone), dextran, dextrin, hyaluronic acid, derivatives of hyaluronic acid, poly(2-hydroxymethyl methacrylate), or mixtures thereof.

28. The coating of claim 1, wherein the second polymer is a polymer having a formula

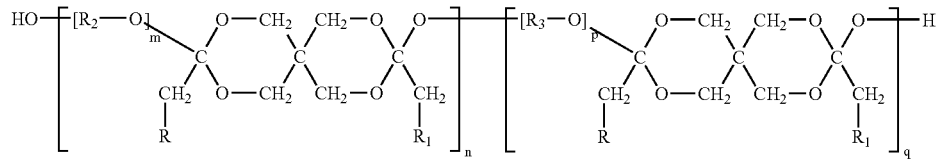

wherein R and R₁, is each, independently, an unsusbstituted or substituted straight-chained, branched, or cyclic alkyl radical $C_1$-$C_8$, unsusbstituted aryl radical, or substituted aryl radical;

$R_2$—O is a non-fouling moiety derived from a hydroxylated functional compound;

$R_3$ is an aliphatic or cycloaliphatic group; and m, n, p, and q are all integers, wherein the value of m is between 5 and 500, the value of n is between 2 and 350, the value of p is between 1 and 20, and the value of q is between 10 and 550.

29. The coating of claim 28, wherein $R_2$ is a poly (methylene oxide structure).

30. The coating of claim 28, wherein the hydroxylated functional compound comprises poly(alkylene glycols), hydroxylated poly(vinyl pyrrolidone), dextran, dextrin, hyaluronic acid, derivatives of hyaluronic acid, poly(2-hydroxymethyl methacrylate), or mixtures thereof.

31. The coating of claim 1, additionally including a third layer comprising a third polymer, the third layer being disposed over at least a portion of the second layer, wherein the third polymer has a higher degree of hydration than the second polymer.

32. The coating of claim 31, wherein the degree of hydration of the third polymer is between greater than 0% and 50% by mass.

33. The coating of claim 31, wherein the third polymer is selected from a group consisting of polyorthoesters, poly (butyleneterephthalate-co-ethylene glycol), poly(ethylene glycol)-block-poly(butyleneterephthalate)-block poly(ethylene glycol), polyorthoesters having poly(ethylene glycol) incorporated into the polymer backbone, copolymers of alkyl methacrylates and 2-hydroxyethyl methacrylate, copolymers of poly(ethylene glycol)-acrylates and alkyl methacrylates, copolymers of poly(ethylene glycol)-methacrylates and alkyl methacrylates, poly(ester-amides) with poly(ethylene glycol) functionality, derivatives of hyaluronic acid, heparin conjugates, sulfonated polystyrenes, and poly(ethylene-co-vinyl alcohol) with pendant poly(ethylene glycol) functionality.

34. The coating of claim 33, wherein the polyorthoesters are products of co-polycondensation of a diketene acetal, a hydroxylated functional compound and a diol.

35. The coating of claim 34, wherein the diketene acetal has a formula

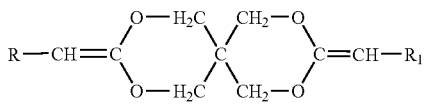

wherein R and R₁ are, independently, unsusbstituted or substituted straight-chained, branched, or cyclic alkyl radicals $C_1$-$C_8$, unsusbstituted aryl radicals, or substituted aryl radicals.

36. The coating of claim 34, wherein the diketene acetal is selected from a group consisting of 3,9-diethylidene-2,4,8,10-tetraoxaspiro-[5,5]-undecane, 3,9-dipentylidene-2,4,8,10-tetraoxaspiro-[5,5]-heptadecane, 3,9-dibutylidene-2,4,8,10-tetraoxaspiro-[5,5]-pentadecane, 3,9-dipropylidene-2,4,8,10-tetraoxaspiro-[5,5]-tridecane, and mixtures thereof.

37. The coating of claim 34, wherein the hydroxylated functional compound comprises poly(alkylene glycols), hydroxylated poly(vinyl pyrrolidone), dextran, dextrin, hyaluronic acid, derivatives of hyaluronic acid, poly(2-hydroxyethyl methacrylate), or mixtures thereof.

38. The coating of claim 37, wherein poly(alkylene glycols) are selected from a group consisting of poly(ethylene glycol), poly(propylene glycol), poly(tetramethylene glycol), and poly(ethylene oxide-co-propylene oxide).

39. The coating of claim 34, wherein the diol comprises alkylene glycols, oligoalkylene glycols, or cycloaliphatic diols.

40. The coating of claim 39, wherein alkylene glycols are selected from a group consisting of ethylene glycol, propane-1,2-diol, propane-1,3-diol, butane-1,4-diol, pentane-1,5-diol, hexane-1,6-diol, heptane-1,7-diol, octane-1,8-diol, nonane-1,9-diol, decane-1,10-diol, undecane-1,1'-diol, dodecane-1,12-diol, tridecane-1,13-diol, tetradecane-1,14-diol, pentadecane-1,15-diol, hexadecane-1,16-diol, butane-1,3-diol, pentane-2,4-diol, hexane-2,5-diol, or mixtures thereof.

41. The coating of claim 39, wherein oligoalkylene glycols are selected from a group consisting of diethylene glycol, trimethylene glycol, tetramethylene glycol, tetraethylene glycol, poly(tetraethylene glycol), poly(propylene glycol), and mixtures thereof.

42. The coating of claim 39, wherein cycloaliphatic diols are selected from a group consisting of trans-cyclohexanedimethanol, 1,4-cyclohexanediol, and mixtures thereof.

43. The coating of claim 31, wherein the third polymer is a polymer having a formula

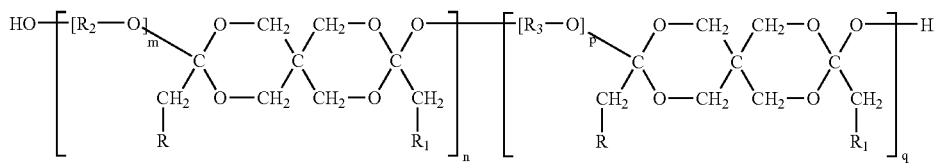

wherein R and $R_1$, is each, independently, an unsusbstituted or substituted straight-chained, branched, or cyclic alkyl radical $C_1$-$C_8$, unsusbstituted aryl radical, or substituted aryl radical;

$R_2$—O is a non-fouling moiety derived from a hydroxylated functional compound;

$R_3$ is an aliphatic or cycloaliphatic group; and m, n, p, and q are all integers, wherein the value of m is between 5 and 500, the value of n is between 2 and 350, the value of p is between 1 and 20, and the value of q is between 10 and 550.

44. The coating of claim 43, wherein $R_2$ is a poly (methylene oxide structure).

45. The coating of claim 43, wherein the hydroxylated functional compound comprises poly(alkylene glycols), hydroxylated poly(vinyl pyrrolidone), dextran, dextrin, hyaluronic acid, derivatives of hyaluronic acid, poly(2-hydroxymethyl methacrylate), or mixtures thereof.

46. A medical article, comprising an implantable substrate and a coating disposed over at least a portion of the substrate, the coating comprising a first layer and a second layer disposed over at least a portion of the first layer, wherein the second layer has a higher degree of hydration than the first layer, and wherein the first polymer or the second polymer comprises a polyorthoester.

* * * * *